United States Patent [19]

MacGregor

[11] Patent Number: 4,627,836
[45] Date of Patent: Dec. 9, 1986

[54] CARDIOVASCULAR PROSTHETIC DEVICES AND IMPLANTS WITH POROUS SYSTEMS

[76] Inventor: David C. MacGregor, 81 Wimbleton Road, Islington, Ontario, Canada

[21] Appl. No.: 486,796

[22] Filed: Jun. 30, 1983

Related U.S. Application Data

[60] Division of Ser. No. 351,526, Feb. 23, 1982, Pat. No. 4,459,252, which is a division of Ser. No. 95,965, Nov. 20, 1979, Pat. No. 4,355,426, which is a division of Ser. No. 824,296, Aug. 15, 1977, Pat. No. 4,281,669, which is a continuation-in-part of Ser. No. 683,382, May 5, 1976, Pat. No. 4,101,984.

[30] Foreign Application Priority Data

| May 9, 1975 | [CA] | Canada | 226993 |
| Dec. 22, 1975 | [GB] | United Kingdom | 52474/75 |
| Aug. 13, 1976 | [CA] | Canada | 259054 |
| Oct. 19, 1976 | [GB] | United Kingdom | 43407/76 |

[51] Int. Cl.$^4$ ............................................. A61M 11/00
[52] U.S. Cl. ..................................... 604/93; 604/891; 604/84; 623/2
[58] Field of Search ............... 3/1.4; 604/890–892, 604/84, 93; 128/334 R; 427/2

[56] References Cited

U.S. PATENT DOCUMENTS

| 3,896,812 | 7/1975 | Kurtz | 604/891 X |
| 4,281,669 | 8/1981 | MacGregor | 128/784 |
| 4,355,426 | 10/1982 | MacGregor | 128/334 R X |
| 4,360,019 | 11/1982 | Portner et al. | 604/891 X |
| 4,378,016 | 3/1983 | Lock | 604/891 |
| 4,479,796 | 10/1984 | Kallok | 604/891 X |

OTHER PUBLICATIONS

Schubert et al., An Impl. Artf. Pancreas, Med. & Bio. Eng. 1980, vol. 18, 1980, 527–537.

*Primary Examiner*—Nancy A. B. Swisher
*Attorney, Agent, or Firm*—Sim & McBurney

[57] ABSTRACT

Novel cardiovascular prosthetic devices or implants having many useful cardiovascular applications comprise a porous surface and a network of interconnected interstitial pores below the surface in fluid flow communication with the surface pores. Tissue forms a smooth thin adherent coating of self-determining thickness on the porous surface making it resistant to the formation of the blood clots normally associated with the presence of foreign bodies in the blood stream. The device has particular utility in heart valves, pacemaker electrodes, blood pumps, blood stream filters, an artificial pancreas, vascular access tubes, small and large bore vascular grafts, blood pump diaphragms and vascular and intracardiac patches.

5 Claims, 17 Drawing Figures

CARDIOVASCULAR PROSTHETIC DEVICES AND IMPLANTS WITH POROUS SYSTEMS

REFERENCE TO RELATED APPLICATION

This application is a division of copending application Ser. No. 351,526 filed Feb. 23, 1982, which is a division of application Ser. No. 95,965 filed Nov. 20, 1979 (now U.S. Pat. No. 4,355,426), which is a division of application Ser. No. 824,296 filed Aug. 15, 1977 (now U.S. Pat. No. 4,281,669), which is a continuation-in-part of application Ser. No. 683,382 filed May 5, 1976 (now U.S. Pat. No. 4,101,984).

FIELD OF INVENTION

This invention relates to novel prosthetic devices and implants for cardiovascular use.

BACKGROUND TO THE INVENTION

It is well known that the introduction of foreign bodies into the blood stream, for example, the polished metal surfaces of artificial heart valves, tends to cause the formation of blood clots which may break loose and embolize to various parts of the body. Such thromboembolic problems have led to the administration of anticoagulants to patients with artificial heart valves. The effects of these anticoagulants on the blood clotting mechanism cause difficulties in stopping the flow of blood through even a minor flesh wound. In addition, flexible plastic conduits are used for vascular graft purposes and such surfaces also are thrombogenic.

Attempts have been made to overcome the thromboembolic problems of polished metal heart valves by providing a porous fabric covering over blood-engaging metal parts. When such porous fabrics have been used for covering metal heart valve parts, pores of typical size 500 to 700 microns have been provided and some tissue ingrowth has been observed. While the fabric covering has resulted in a decreased incidence of thromboembolism, apparently due to the observed tissue ingrowth, such valves do suffer from other defects, notably wear of the fabric, causing cloth fragment embolism and chronic hemolytic anemia as a result of turbulence of the blood over disrupted fabric coverings.

To date, the prior art has been unable to provide a heart valve which not only overcomes the thromboembolic problems of a smooth metal surface but also does not exhibit the wear failure problem of the prior art fabric covered heart valves.

SUMMARY OF THE INVENTION

The present invention is directed to cardiovascular prosthetic devices or implants comprising a porous surface and a network of interconnected interstitial pores below the surface in fluid flow communication with the surface pores. The provision of the porous surface and subsurface network promotes the formation of a smooth thin adherent tissue coating on the porous surface rendering the same resistant to the formation of blood clots normally associated with the presence of foreign bodies in the blood stream.

The formation of the adherent tissue coating on the porous surface also allows the cardiovascular prosthetic device or implant of the present invention to be incorporated into the cardiovascular system, thereby achieving a more secure attachment than has previously been the case.

The tissue coating is formed by colonization of nucleated cells circulating in the blood stream onto the porous surface and subsequent differentiation into other cell types. The tissue coating is formed rapidly over about a one-month period, does not appear to increase significantly in thickness thereafter and includes flattened endothelial-like cells at the surface thereof.

GENERAL DESCRIPTION OF INVENTION

In U.S. Pat. No. 3,855,638, there is described a surgical prosthetic device consisting of a metal substrate with a porous metal coating into which bone tissue may grow for incorporation of the prosthesis into the body. The porous coating used in this prior art device has several essential requirements, including restrictions on coating thickness, interstitial pore size and coating porosity. These parameters are dictated by the strength requirements of the surgical prosthetic device, namely, that the coating and the coating-substrate interface have strengths at least that of bone, so that there is no danger of failure of the prosthesis after ingrowth of bone tissue.

In cardiovascular uses, however, strength is a less important consideration, and the ranges of parameters chosen are dictated to some degree by the intended use of the prosthetic device or implant.

Further, the mechanism of incorporation of the surgical prosthetic device of this prior art into the body is by ingrowth of tissue into the coating while the present invention involves quite a different mechanism which arises from the different environment of the devices of the invention as compared with that of the prior art.

The cardiovascular devices and implants provided in accordance with this invention fall broadly into two classes, namely, rigid items and flexible polymeric items, although there may be overlap between the classes, as described in more detail below. For convenience, the specific embodiments of the invention will be described within the general framework of the two broad classes.

A. CARDIOVASCULAR DEVICES AND IMPLANTS CONSTRUCTED OF RIGID MATERIAL

The material of construction of the items in this class usually is a metal although other materials of construction may be used, such as, rigid polymeric material, ceramic material and carbon. Combination of two or more of the materials of construction may be used.

The general parameters of the porous surface for use in this class of cardiovascular devices and implants of this invention may vary widely and those chosen depend somewhat on the particular end use of the prosthetic device or implant, and specific parameters for certain specific devices or implants are discussed in more detail below.

The porous surface intended to engage blood must have an interconnected network of pores beneath the surface in fluid flow communication with the surface pores to promote the colonization by nucleated cells and subsequent differentiation into other cell types so that the tissue which is formed and grows into the surface is interlocked in the subsurface network rendering the surface non-thrombogenic. The network of pores preferably extends substantially throughout the body of the porous system.

The interstitial pore size may vary widely, generally from about 1 micron up to about 1000 microns, although it may be preferred to use pore sizes below about 20 microns. The porosity also may vary widely, generally from about 8% by volume to the limit of coherence of the porous surface, and usually in the range of about 10 to about 50% by volume.

The porous surface may be provided as part of a composite of a porous coating embodying the surface on a coherent substrate in certain embodiments of the invention, although a wholly porous structure may be used. The thickness of the porous coating may vary from double layers of particles upwards, generally from about 1 to about 10,000 microns, thin layers being preferred in devices having close tolerances.

The cardiovascular devices and implants should have adequate strength to maintain their structural integrity under the physiological stresses of the environment in the body.

The materials of construction of the cardiovascular devices and implants in this class of items should be non-toxic to blood and body tissue and be otherwise biocompatible. This class of items will be described particularly with reference to metals, the term "metal" as used herein including metal alloys, although it is understood that the parameters described with respect to metals apply generally equally with respect to the other materials of construction.

One suitable metallic material of construction is the cobalt alloy that is known by the trade mark "VITALLIUM" while a further suitable material is titanium.

The metal devices and implants in this class may be in the form of or include a rigid wholly porous system intended to engage blood and in which a network of interconnected pores extends substantially uniformly throughout the body of the system and is defined by metallic particles joined to adjacent particles.

Alternatively, the metal devices and implants may include a rigid composite of a dense coherent metallic substrate and a rigid metallic porous coating intended to engage blood and which is adhered to the substrate and consists of metallic particles joined to adjacent particles to form an interconnected network of pores which is substantially uniformly distributed throughout the coating.

The rigid nature of the porous coating or porous system, the strength of the particle-particle bond and the strength of the substrate-coating interface in the case of the composite provide excellent wear and strength characteristics in the cardiovascular implant or device. The precise parameters of the porous coating or system vary depending on the form of the device or implant, and specific values are discussed below in connection with the specific embodiments of this class of item.

Metal particles making up the porous coating or system usually have a regular geometrical shape, such as spherical, but irregularly-shaped particles alone, or in admixture with regularly-shaped particles, may be used.

SPECIFIC EMBODIMENTS OF RIGID CARDIOVASCULAR DEVICES AND IMPLANTS

1. Heart Valve Embodiment

One specific embodiment of the invention is a heart valve. Heart valves include a plurality of components including an occluder, typically a ball or disc which may be rigid or flexible, an occluder seating ring, occluder guide struts, optionally muscle guards to prevent interference by muscle with movement of the occluder, and a sewing ring to attach the valve to the heart. The occluder seating ring, occluder guide struts and muscle guards usually are constructed of metal. The occluder may be metal or other material.

In accordance with this invention, the metallic blood engaging elements of a heart valve are formed as composites of the type described above and having a dense coherent metallic substrate and a rigid metallic porous coating which is adhered to the substrate.

It is usual, however, to provide a polished metal surface in those blood-engaging portion of the valve where blood movement is sufficient to prevent the incidence of thrombus formation, such as, adjacent to the occluder, where engagement between the occluder and other parts may occur and where tissue growth may interfere with occluder movement.

The proportion of the blood-engaging elements of the heart valve from which the porous coating is omitted varies depending on the design of the heart valve but generally constitutes only a minor proportion of the blood-engaging elements.

The coating should be formed from fine metallic particles, usually of −325 mesh size and preferably of −500 mesh size, in order to minimize abrasion between heart valve elements and hemolysis of the blood. It has been found that porous coatings formed from finer particles provide smoother tissue coatings than porous coatings formed from coarser particles.

It is also preferred to provide a thin porous coating on the metal substrate surfaces in order to provide the maximum orifice for blood flow, and typically the thickness is about 20 to 300 microns, preferably about 50 to about 150 microns.

The shear strength of the composite surface is important, especially where heart valve surfaces are in relative motion, and it is necessary that the composite have a high fatigue tolerance, the endurance limit ($10^7$ cycles) being greater than 500 psi. It is preferred for the surface-coating interface and the coating itself to have shear strengths greater than about 1000 psi, more particularly greater than about 3000 psi.

The porosity of the coating portion of the composite varies between about 10 and about 50% by volume. Equivalent parameters are employed for other materials of construction.

The suture or sewing ring used in rigid metallic valves, particularly those having the characteristics described above, may be provided in the form of a flexible polymeric material having a porous surface interconnecting with a network of interconnected pores in the subsurface. This structure represents one overlap between the classes of structure provided in accordance with this invention.

The porous polymeric material may be provided as the outer surface of a conventional foam filled fabric covered suture ring, attached thereto directly or through an intermediate solid substrate.

It is preferred, however, to utilize a composite of the porous polymeric material and a coherent polmeric substrate as the sewing ring by providing direct attachment between the polymeric substrate and the occluder seating ring.

The attachment may be achieved by causing the solid substrate to flow into a porous metal surface formed on the seating ring and harden in the subsurface pores to interlock with the network of interconnected pores, for example, by pressure molding.

The latter procedure may be used, if desired, to provide flexible or rigid solid and/or porous plastic material coatings on rigid metal coatings or other heart valve components, by pressure molding a polymer to the metal coating.

Where a porous polymeric sewing ring is provided in accordance with the above-described structure, the interstitial pore size is generally less than 200 microns while the porosity is about 10 to about 50% by volume.

2. Pacemaker Electrode Embodiment

Another specific embodiment of the invention is a pacemaker electrode which is intended especially for location in the heart in engagement with blood and tissue within the heart and for subjecting the heart to timed electrical impulses fed from a remote pacemaker.

As described in more detail below, electrodes of the type here described may also be used for electrical stimulation of the central or peripheral nervous system and body muscles.

In this specific embodiment, the pacemaker electrode preferably takes the form of a composite of the above described form, comprising a dense coherent metal substrate and a rigid porous metal coating which is adhered to the substrate. Electrodes which are wholly porous also may be provided.

The particles in the metallic coating generally have a particle size of about $-100$ mesh, preferably about $-325$ mesh and more preferably $-500$ mesh. The coating has a porosity of about 10 to about 50% by volume and the surface-coating interface and the coating itself have a shear strength of greater than about 1000 psi to ensure adequate structural strength.

The thickness of the coating may vary widely up to about 500 microns, although a thickness in the range of about 20 to about 300 microns is preferred. Equivalent parameters are employed for other materials of construction.

A portion of the porous metal coating may be utilized to bond to the electrode a polymer sleeve surrounding the current conducting wire. This bonding may be achieved by causing the sleeve polymer to flow into the porous metal surface and harden in the subsurface pores to interlock with the network of interconnected pores, for example, by pressure molding.

In some cases, it may be desirable to provide an outer polymeric coating, preferably a coating of a hydrophilic polymer having a porous surface on the porous tip surface, rather than have the porous metal coating exposed to blood and tissue. This polymeric coating may be provided by the technique described above for joining the sleeve to the electrode, for example, by pressure molding. If desired, the polymer coating may have a porous outer surface.

The electrode provided in accordance with this embodiment of the invention may be in the form of a differential current density electrode. Electrodes of this type generally consist of a metal current-carrying electrode surrounded by an insulating polymeric sleeve which is spaced from a cylindrical end portion of the electrode to define an electrolyte-containing chamber. A small number of holes extend through the polymer sleeve to the electrolyte-containing chamber.

This type of electrode achieves a very high current density at several points on the surface thereof corresponding to the holes through the sleeve while utilizing a very low current density on the metal electrode, thereby achieving the high current density required for efficient pacing while exerting only a low energy drain on the pacer battery.

In accordance with this invention, the surface of the polymer sleeve consists of an outer porous layer on a dense coherent substrate, permitting tissue formation and growth into the polymer sleeve. The polymer sleeve also may be joined to the metal electrode in the non-spaced apart regions by using the technique described above for joining a polymer sleeve to a metal electrode, for example, by pressure molding.

The outer porous coating of such a differential current density electrode may have a thickness up to about 500 microns, although a thickness in the range of 20 to about 300 microns is preferred. The interstitial pore size is generally less than 200 microns with a coating porosity of about 10 to about 50% by volume.

Alternative structures of this type of electrode provide a wholly porous cylindrical metal electrode portion in the electrolytic chamber and the provision of the outer sleeve in contact with the outer surface of a wholly porous cylindrical metal electrode portion containing electrolyte.

3. Blood Pump Embodiment

Another device utilizing a composite of the above described type comprising a coherent substrate having an adherent porous coating over the blood engaging surfaces thereof is a partially or totally implantable blood pump, such as, an artificial heart or ventricular assist device.

A blood pump generally possesses a housing having an inlet and an outlet, valves located in the inlet and outlet to control the flow of blood into and out of the housing and means for varying the internal volume of the housing to achieve pumping motion from the inlet to the outlet. The valves may be of the character and type already described above while the housing used is constructed of metal. The volume varying means preferably is a flexible diaphragm, described in more detail below with respect to the class of flexible items.

In this embodiment, the porous metal coating usually has a thickness of less than about 500 microns, preferably about 25 to about 300 microns. The particles forming the coating usually have a size of about −100 mesh, preferably −325 mesh, and more preferably −500 mesh.

The metal coating has a porosity of about 10 to about 50% by volume and the surface-coating interface and the coating itself has a shear strength of greater than about 1000 psi to ensure adequate structural strength.

Equivalent parameters are employed for other materials of construction.

4. Blood Stream Filter Embodiment

A further embodiment of this invention is a blood stream filter which is constructed to prevent the passage therepast of blood clots present in the blood stream.

Such filters generally are constructed of metal and comprise a filter medium and support structure. In accordance with this invention, the blood engaging surfaces of the filter are formed of a composite of a dense coherent metal substrate and a rigid metallic porous coating which is adhered to the substrate.

The porous coating is usually formed of particles of size about −100 mesh, preferably −325 mesh. The thickness of the coating on the substrate surface may vary widely up to about 500 microns, although it is preferred to employ a thickness of about 25 to about 300 microns.

The coating generally has a porosity of about 10 to about 50% and the surface-coating interface and the coating itself has a shear strength of greater than about 1000 psi to ensure adequate structural strength.

Equivalent parameters may be employed with other materials of construction.

5. Blood Stream Release Control Embodiment

The blood-engaging porous system provided in this invention may be used to sample non-cellular material therethrough for the detection of the presence and/or concentration of the constituents and/or for the conveying of material into the blood through the porous system.

In accordance with this embodiment, an artificial endocrine organ, such as an artificial pancreas, may be provided.

The artificial pancreas possesses a chamber having a porous surface intended to interface with the blood and communicating with the interior of the chamber. The chamber may contain pancreatic islet cells for discharging insulin and/or glucagon to the blood stream through the porous surface. A semi-permeable membrane is located between the porous surface and the cells within the chamber to prevent biological rejection by the body.

Alternatively, the chamber may contain sensing devices and release mechanisms permitting glucose to be sampled through the porous system interfacing with the flowing blood and insulin and/or glucagon to be released through the porous system and the tissue coating thereon into the flowing blood. The source of the hormones and/or the control circuitry and/or the energy sources may be provided external to the body, if desired, or may be implanted.

In accordance with this embodiment, a slow release device also may be provided having a porous surface interfacing blood and communicating with a hollow interior containing a substance to be released through the surface. Such a device provides slow, sustained release of the substance into the blood through the porous system and its associated tissue coating interfacing the blood. The contents of the chamber of the device may be separated from the porous surface by a semipermeable membrane as an aid in controlling the release of the substance. The substance may be a drug, for example for long term antibiotic therapy, or hormones, for example, steroids providing a chronic implanted birth control device.

In the wholly porous system provided in such devices, the interstitial pore size may vary widely, for example, from about 1 micron up to about 1000 microns. The porosity of the porous system may also vary widely, upwardly from about 8%, and usually in the range of about 10 to about 50%.

The thickness of the porous system is not critical and may vary widely, for example, up to about 1 cm, although a thickness in the range of about 25 to about 500 microns usually is adopted.

Equivalent parameters are used for other materials of construction.

6. Vascular Access Tubes

The blood engaging portions of vascular access tubes may be formed of a composite of a dense coherent substrate and a rigid porous coating which is adhered to the substrate, in accordance with a further specific embodiment of the invention.

Such vascular access tubes generally are metal, although rigid or flexible plastic materials also may be used. The access tubes may be positioned wholly subcutaneously or transcutaneously as desired.

The particles in the metal coating generally have a particle size of about −100 mesh, preferably −325 mesh and more preferably −500 mesh. The coating has a porosity of about 10 to about 50% by volume and the surface-coating interface and the coating itself have a shear strength of greater than about 1000 psi to ensure adequate structural strength.

The coating may have a thickness which varies widely up to about 500 microns, a thickness in the range of about 20 to about 300 microns being preferred. Equivalent parameters are employed with other materials of construction.

MANUFACTURE OF COMPOSITE STRUCTURE IN METAL DEVICES AND IMPLANTS

The composite structure of many of the metal cardiovascular devices or implants provided in accordance with this invention is formed by a sintering procedure, in which a multiple number of layers of particles are simultaneously formed on the substrate. Additional multiple layers may be formed by further sintering.

The procedure involves roughening the smooth coherent substrate surface where the coating is to be formed, forming a self-supporting coating of a plurality of layers of metallic particles bound together and to the substrate by a suitable adhesive, drying the binder to provide a preform of dried coating on the substrate, and sintering the preform to cause metal fusion interconnection of the metal particles one with another and with the roughened metal substrate.

In an alternative procedure, the preform may be formed from particles of a metal compound which is readily thermally decomposable or a mixture of such compounds and such particles which thermally decompose during the sintering step to provide the interconnection of the metal particles with each other and to the substrate on sintering.

The precise sintering technique adopted depends to some extent on the size of the particles from which the porous coating is formed and whether the particles are in metal or metal compound form. The metal of the substrate and of the porous coating usually are the same, although different metals may be used, if desired.

The metal and metal compound particles from which the porous coating is formed generally fall into one of four categories, namely $-500$ mesh (less than about $20\mu$), $-325+500$ mesh (about 20 to about $50\mu$), $-100+325$ mesh (about 50 to about $200\mu$) and $+100$ mesh (greater than about $+200\mu$). The term "mesh" used herein refers to the U.S. Standard Sieve mesh size.

The initial roughening of the smooth coherent substrate may be carried out in any convenient manner, for example, by blasting with abrasive material. Thereafter, the coating of particles is formed on the surface.

In one procedure, a binder for the particles first is sprayed onto the roughened metal surface and the device then is suspended in a fluidized bed of powder metal particles or powder metal compound particles to form a coating on the roughened surface. The coated body is withdrawn from the fluidized bed and the binder allowed to dry. This procedure has been found to be satisfactory for each of the particle sizes, except for the $-500$ mesh particles.

In an alternative procedure, the powder metal or metal compound particles are mixed with a binder to form a fairly viscous slurry which is spray applied to the roughened surface to form the coating thereon, the coating thereafter being dried. It has been found that this procedure is satisfactory for $-325$ mesh size particles and below.

In a further procedure, the metal or metal compound particles and binder are slurried and the roughened surface is dipped into the slurry. Excess material is allowed to run off and the coated body is dried.

Other methods of powder application may be adopted.

In each case, where the coating is formed from metal particles, after the formation of the dried coating on the substrate, the preform of dried coating and substrate is sintered to cause metal fusion interconnection of the metal particles one with another and with the roughened substrate surface to provide a rigid porous structure consisting of multiple layers of particles having a network of interconnected pores substantially uniformly distributed throughout the coating.

It is possible to build up any desired thickness of porous coating on the coherent substrate by presintering the dried coating to provide some strength thereto and then repeating the coating and presintering operation for as many cycles as is required to build up the desired thickness. Each layer formed on the substrate contains a plurality of layers of particles. When the desired thickness has been achieved, the composite is sintered to provide the required particle-particle and particle-substrate bonds.

The presintering and sintering temperatures which are preferably utilized depend on the particle size of the metal particles, lower temperatures generally being used for smaller particle sizes.

Thus, for $-500$ mesh metal particles, presintering preferably is carried out by heating at a temperature of about 2000° F. (about 1100° C.) momentarily or up to about 10 minutes and then cooling. Then, sintering preferably is carried out by heating at a temperature of about 2150° F. (about 1175° C.) for about 60 to about 90 minutes in a hydrogen or other reducing gas atmosphere, or under vacuum.

For the $-325+500$ mesh metal particles, presintering preferably is carried out by heating at a temperature of about 2100° F. (about 1150° C.) for about 8 minutes, while sintering preferably is carried out by heating at a temperature of about 2200° F. (about 1200° C.) for about 60 to about 90 minutes in a hydrogen or other reducing gas atmosphere, or under vacuum.

When metal particles of particle size $+325$ mesh are used, the presintering preferably is carried out at a temperature of about 2200° F. (about 1200° C.) and sintering preferably is carried out at a temperature of about 2200° to about 2300° F. (about 1200° C. to about 1250° C.) for about 2 to about 3 hours, in a hydrogen or other reducing gas atmosphere, or under vacuum.

In the case where the coating is formed from thermally-decomposable metal compound particles, the preform is heated to an elevated temperature to cause thermal decomposition of the metal compound and the formation of a porous coating of metal particles which are connected together at their points of contact with each other and the substrate to define a network of interconnected pores substantially uniformly distributed throughout the coating.

The technique described above for the building up of layers of particles to the required thickness may be adopted. The presintering and sintering temperatures which are preferably utilized correspond generally to those for metal particles of the same size.

The use of metal compounds in the sintering process is especially beneficial in those instances where particles of the metal itself cannot be used at the desired particle size for any particular reason. For example, certain metals, such as titanium, are pyrophoric at small particle sizes.

Non-pyrophoric thermally-decomposable metal compounds, such as, the hydrides of those metals, then are used in place of the metal. This procedure is particularly useful for making cardiovascular devices or implants of titanium by thermal decomposition of titanium hydride particles on the metal substrate, for example, particles of $-500$ mesh.

Vacuum is usually used to withdraw the gas formed during the thermal decomposition of the metal compound.

Following formation of the porous coating utilizing the above techniques, the coating may be machined and refined, if desired, to improve its surface characteristics.

PRODUCTION OF WHOLLY POROUS METAL SYSTEMS

Wholly porous metallic devices and implants provided in accordance with this invention may be formed by sintering metal particles or metal compound particles in a mold at the sinter temperatures described above for the formation of porous coating layers, along with binders, if necessary.

DESCRIPTION OF HEART VALVE PHOTOGRAPHS— FIGS. 1 TO 4

Figure 1:
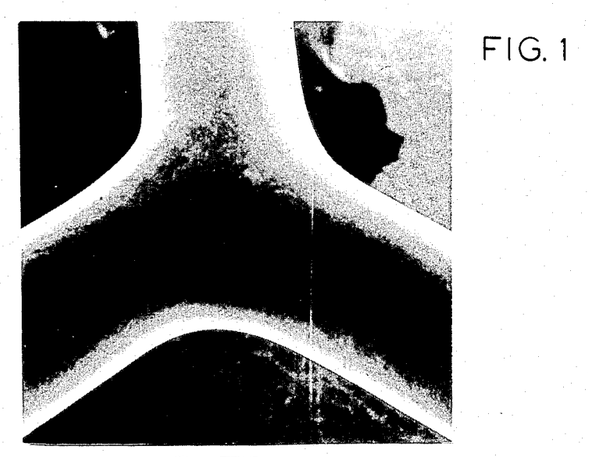
FIG. 1 is a photograph of uncoated metal strut members of a heart valve cage at 25 times magnification.
Figure 2:
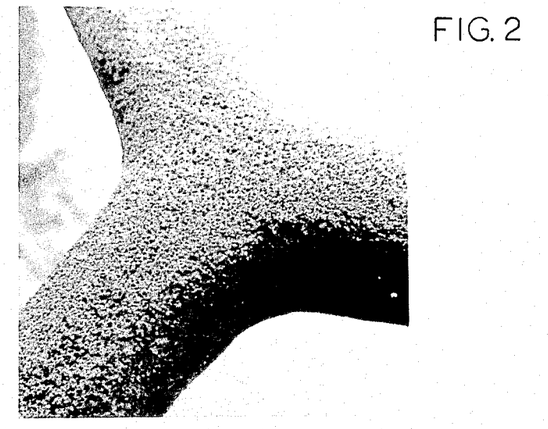
FIG. 2 is a photograph of the strut members in FIG. 1 coated with −500 mesh metallic powder at 25 times magnification.
Figure 3:
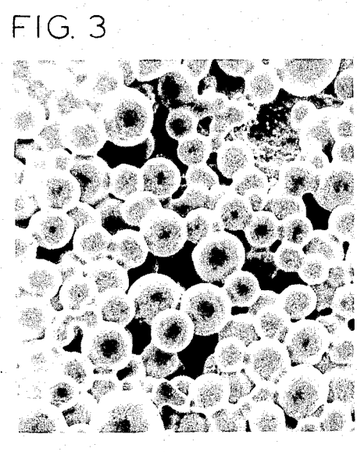
FIG. 3 is a close-up photograph of the surface of the coating of FIG. 2 at 750 times magnification.
Figure 4:
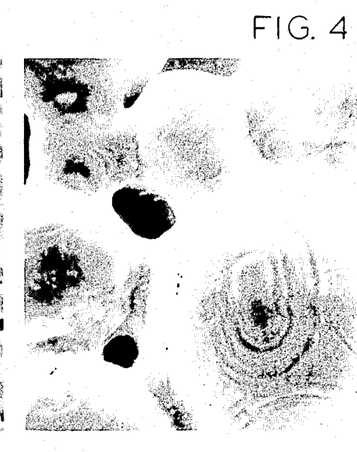
FIG. 4 is a close-up photograph of the surface of the coating of FIG. 2 at 3500 times magnification.

In FIGS. 1 to 4, there are illustrated uncoated metal heart valve struts (FIG. 1) and the same heart valve struts coated with −500 mesh metallic powder using the above described techniques at various magnifications (FIGS. 2 to 4).

Figure 5:
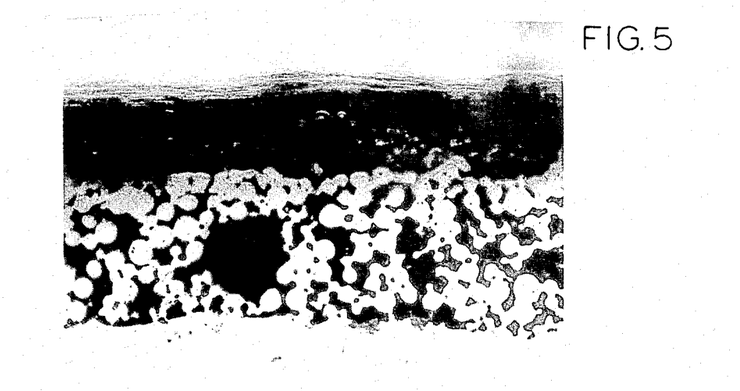
FIG. 5 is a thin section taken through a porous coated metal heart valve element after positioning in the blood stream of a dog for 2 months at 300 times magnification showing the formation and ingrowth of smooth-surfaced endothelialized tissue on the porous surface.

The normal polished metal surface struts (FIG. 1) of a heart valve cage, the apex of which is seen in FIGS. 1 and 2, is coated with an adhered rigid porous coating of substantially spherical metal particles, giving the struts the appearance seen in FIG. 2. In the highly magnified photographs of FIGS. 3 and 4, it can be seen that the metal particles are adhered one to another by diffusion bonded regions to define a plurality of surface pores. The surface pores communicate with a subsurface interconnected network of interstitial pores, as may be seen from the thin section of FIG. 5.

B. CARDIOVASCULAR DEVICES AND IMPLANTS CONSTRUCTED OF FLEXIBLE POLYMERIC MATERIAL

Flexible porous polymeric materials are used to provide the cardiovascular device or implant of this class. The polymeric material used is a biocompatible synthetic polymeric material, preferably a segmented polyurethane and more preferably a segmented hydrophilic polyurethane.

The general parameters of the porous surface for use in this class of cardiovascular devices and implants of this invention may vary widely and those chosen depend somewhat on the particular end use of the prosthetic device or implant, and specific parameters for certain specific devices or implants are described in more detail below.

The porous surface of the flexible polymeric material must have an interconnected network of pores beneath the surface in fluid flow communication with the surface pores to promote the colonization by nucleated cells and subsequent differentiation into other cell types so that the tissue which is formed and grows into the surface is interlocked in the subsurface network and renders the surface non-thrombogenic. The network of pores is preferably substantially uniformly distributed throughout the porous system.

The porous surface may be provided as part of a composite of a porous coating embodying the surface and subsurface network on a coherent substrate in some embodiments while a wholly porous structure may be used in other embodiments.

SPECIFIC EMBODIMENTS OF FLEXIBLE POLYMERIC MATERIAL CARDIOVASCULAR DEVICES AND IMPLANTS

1. Small Bore Vascular Grafts

Small bore vascular grafts comprise an elongate tubular body having an inside diameter from about 2 to about 6 mm, the diameter generally corresponding to the diameter of the vessel to which the tube is to be grafted. The wall thickness of the graft may vary widely from about 0.2 mm to about 1 mm or more.

The vascular grafts may be in the form of a single tube length or may have one or more integral branches to conform with the anatomical requirements of the graft.

The inner blood-engaging surface of the graft is porous and communicates with a network of interconnected pores in the subsurface region. The interconnected pores preferably are substantially uniformly distributed throughout the subsurface region. The pore size in the surface and the subsurface region is generally less than about 50 microns and preferably less than about 20 microns. The internal porosity promotes the formation of tissue on the surface, as described above in connection with the rigid items provided in accordance with this invention.

The outer surface of the graft also is porous and communicates with a network of interconnected pores in the subsurface region, permitting ingrowth of soft tissue from the surrounding body tissue, to incorporate the graft permanently into the body.

The interstitial pore size of the outer porous region of the graft may be the same as that of the inner porous region, but the pore sizes also may vary and in the outer porous region, pore sizes of up to about 200 microns may be used.

The porosity of the inner and outer porous regions of the graft may vary from about 10 to about 70 vol.% consistent with the interconnected porosity requirement for the subsurface regions.

The graft is required to have a minimum strength in use consistent with the requirements that the graft may be sutured readily without tearing and that the graft have sufficient strength to prevent structural breakdown at the anastomosis and along the length of the graft.

The actual minimum strength requirements will vary depending on the intended use of the graft, the strength requirements for venous grafts being very much less than those for arterial grafts because of the lower venous blood pressures. The grafts provided in accordance with this embodiment of the invention for venous use should be able to withstand venous blood pressure of not less than 25 mm Hg for prolonged periods, generally greater than one year, preferably greater than 5 years, in a physiological environment.

The preferred aspect of this embodiment of the invention is the provision of an arterial graft, which also may be used as a venous graft, if desired, and such an arterial graft should be able to withstand pulsatile arterial blood pressure of greater than about 300 mm Hg, preferably greater than about 500 mm Hg, for a prolonged period fo time, generally greater than one year, preferably greater than 5 years, in a physiological environment.

Consistent with these minimum strength requirements, the graft may have a wholly porous wall having a uniform pore size throughout, or a wholly porous wall in which the pore size varies in the inner and outer surface regions. Additionally, a dense coherent flexible polymeric substrate layer may be laminated between inner and outer porous layers.

In one preferred structure of the vascular graft, reinforcing material is provided in association with the porous wall, and such reinforcing material preferably takes the form of a fabric layer, such as a knitted Dacron fabric layer laminated between inner and outer porous layers, although fibres, platelets and fillers also may be used as reinforcing agents.

2. Large Bore Vascular Grafts

Large bore vascular grafts differ from the small bore vascular grafts described above in having an inside diameter greater than about 6 mm up to about 10 cm, although it is preferred for such grafts to have an inside diameter of less than about 5 cm.

The large bore vascular grafts also differ from the small bore grafts in that the pore size of blood engaging surface and associated subsurface region may vary up to about 200 microns, if desired, although it is preferred to utilize the smaller pore size of less than 50 microns and more preferably less than 20 microns.

The porosity and strength requirements of the large bore graft are the same as those for the small bore graft referred to above. Additionally, in common with the small bore grafts, the large bore grafts may be provided as a single tube or as a branched tube having one or more integral branches. Further, large bore grafts may be provided with one or more integral small bore branches, if desired.

3. Blood Pump Diaphragms

As described above in connection with the structure of blood pumps, a flexible diaphragm is generally used to achieve the internal volumetric changes required to convey the blood through the pump.

In accordance with this embodiment of the invention, a blood pump diaphragm is provided in the form of an appropriately dimensioned planar sheet of flexible polymeric material having a porous surface intended to engage blood in the pump and in fluid flow communication with a network of interconnected pores in a subsurface region. The wall thickness of the diaphragm may vary widely from about 0.2 mm to about 1.0 mm or more. The interconnected pores are preferably substantially uniformly distributed throughout the subsurface region.

The porosity promotes the formation of tissue on the porous surface, as described in detail above in connection with rigid items provided in accordance with this invention.

The pore size in the surface and the subsurface region is less than about 200 microns, preferably less than about 50 microns and more preferably less than about 20 microns, while the porosity may vary from about 10 to about 70 vol. %.

The diaphragm is required to have a minimum strength to prevent structural breakdown with use and to this end the diaphragm when positioned in the blood pump and the latter is located in a physiological environment, should be able to withstand pulsatile arterial blood pressure of greater than about 300 mm Hg, preferably greater than about 500 mm Hg, for a prolonged period of time, generally greater than one year and preferably greater than about 5 years.

The diaphragm may be provided with a wholly porous structure or more usually is formed as a composite of a porous coating which engages the blood bonded to a coherent flexible polymeric substrate.

The diaphragm also may have a porous subsurface region in which reinforcement is provided, such as a layer of a fabric bonded to or within a porous layer.

4. Vascular And Intracardiac Patches

Vascular and intracardiac patches provided in accordance with this embodiment of the invention take the form of a planar sheet of flexible polymeric material having a porous surface intended to engage blood in use and in fluid flow communication with a network of interconnected pores in a subsurface region, which are preferably substantially uniformly distributed throughout the subsurface region.

Porous surfaces generally are provided on both sides of the patches. In the case of the vascular patches, one side of the patch engages the blood to promote tissue ingrowth thereon while the other side engages surrounding body tissue to promote ingrowth of soft tissue.

In the case of the intracardiac patches, blood engages both sides of the patch within the heart and tissue grows on both sides from the blood. The wall thickness of the vascular and intracardiac patches may vary widely from about 0.2 mm to about 1.0 mm or more.

The pore size in the surfaces and the subsurface regions is less than about 200 microns, preferably less than about 50 microns, more preferably less than about 20 microns, while the porosity may vary from about 10 to about 70 vol. %. Generally, the porosity is the same on both sides of the patches, but may be varied, if desired.

The patch is required to have a minimum strength in use consistent with the requirements that the patch may be sutured readily without tearing and that the patch have sufficient strength to prevent structural breakdown at the suture lines and over the area of the patch.

The minimum strength requirements of the patch will vary depending on its intended use. Thus, where the vascular patch is intended for venous repair use only, the strength requirements are less than for vascular patches which are intended for arterial repair use and for intracardiac patches.

The vascular patches intended for venous use should be able to withstand venous pressure of not less than 25 mm Hg for prolonged periods, generally greater than one year and preferably greater than 5 years in a physiological environment, while the vascular patches intended for arterial use and the intracardiac patches should be able to withstand pulsatile arterial pressure of not less than about 300 mm Hg, and preferably not less than about 500 mm Hg, for a prolonged period of time, generally greater than one year, preferably greater than 5 years, in a physiological environment.

Consistent with these minimum strength requirements, the patch may be wholly porous with a uniform pore size throughout or may be wholly porous with differing pore sizes in different regions. Additionally, a dense coherent flexible polymeric substrate layer may be laminated between two porous face layers.

Preferably, a reinforcing material is provided in association with the porous material. Such reinforcing material preferably takes the form of a fabric layer, such as, a knitted Dacron fabric layer, laminated between two porous face layers, although fibres, platelets and fillers also may be used as reinforcing agents.

5. Flexible Heart Valve Occluders

Some heart valves employ flexible occluders, generally in the form of flaps, and in accordance with another embodiment of the invention, such flap-type occluders take the form of an appropriately-dimensioned planar sheet of flexible polymeric material having porous surfaces intended to engage blood in use and in fluid flow communication with networks of interconnected pores in subsurface regions.

The planar sheet may be wholly porous with the interconnected pores substantially uniformly distributed through the sheet or in the form of a laminate of two outer porous layers bonded to an inner coherent flexible polymeric layer. A reinforcing material may be provided in association with the porous material, preferably in the form of a fabric layer, such as, a knitted Dacron fabric layer, laminated between two porous face layers.

The pore sizes in the porous structure is less than about 200 microns, preferably less than about 50 microns, and more preferably less than about 20 microns, while the porosity may vary from about 10 to about 70%.

The flap is required to have a minimum strength in use consistent with the requirements that the flap may be assembled with the remainder of the heart valve without tearing and that the flap have sufficient strength to prevent structural breakdown in use. The wall thickness of the flap may vary widely from about 0.2 mm to about 1.0 mm or more.

PRODUCTION OF POROUS STRUCTURE IN POLYMERIC DEVICES AND IMPLANTS

A number of procedures may be used to produce polymeric cardiovascular devices and implants having a porous structure therein according to this invention, either in rigid or flexible polymeric form.

The preferred procedure for forming the porous polymeric structure is to uniformly disperse solvent-elutable particles in a continuous or discontinuous polymer phase, form a coherent shaped article from the dispersion wherein solvent-elutable particles are substantially uniformly dispersed throughout a continuous solid polymer phase in generally intraparticulate contact, and elute the solvent-elutable particles from the article to provide a porous shaped product having interconnected pores therein.

The above-described porous polymer forming procedure may be effected in a number of different ways, the particular one chosen depending on the shape of product desired, the nature of the polymer used and the form of the product desired. One such procedure involves pulverizing a rigid polymer to the desired particle size, mixing the powder with the solvent-elutable particles, compressing the mixture, molding or extruding the mixture to the desired shape and leaching the solvent elutable particles from the coherent shaped article to remove the solvent-elutable particles.

Another specific procedure involves blending together a moldable and/or extrudable polymeric material and solvent-elutable particles in sufficient quantities to provide a continuous phase of polymer and a dispersed phase of solvent-elutable particles in the blend. Thereafter, the blend is molded or extruded to the desired shape and contacted with solvent to remove the solvent-elutable particles and leave an open network of interconnected pores throughout the body.

In a modification of this procedure, the polymer may be provided as a solution into which the solvent elutable particles are mixed. After removal of the solvent, the molding or extruding and leaching operations are carried out.

Yet another specific procedure for forming the microporous polymer product involves initial formation of beads of polymer having a core of solvent-elutable material by polymer solution coating of the core material, compression molding or extruding of the beads to the desired shape and product leaching to remove the solvent-elutable material.

A further specific procedure for the formation of a microporous polymeric product includes forming a viscous casting solution of the polymer, dispersing the solvent-elutable particles in the solution, casting the solution onto a casting surface and, after removal of solvent, eluting the solvent-elutable particles from the cast material.

Where it is desired by this procedure to form a porous tubular body, for example, for use as a flexible blood vessel graft, the viscous casting solution is placed in a tube of inside diameter corresponding to the outside diameter of the desired tube. A plumb ball or other suitable device, such as a rod, of diameter corresponding to the inside diameter of the article desired is drawn through the column of viscous material, resulting in the casting of the polymer on the inside of the tube.

Following drying of the casting, the polymer tube is removed, and the particles eluted to provide the porous structure. Following the elution step, the structure of the device, including its porosity, may be modified by heat treatment, such as, in an autoclave.

The porous polymeric structure formed by these procedures may be used as such or in a lamination or composite structure with one or more coherent solid rigid or flexible polymer substrates. Such composites or laminates may be formed by conventional techniques, using suitable bonding between the porous material and the substrate.

Where it is desired to provide reinforcement to the porous material, such as, by way of a knitted fabric, as described above, such material may be incorporated into the structure by suitable modification to the porous structure-forming procedure.

COMBINATION WITH SOFT TISSUE INGROWTH

In many applications of the present invention, the promotion of colonization and tissue growth is accompanied by true soft tissue ingrowth into the porous surface at the margins or on the outer surface from adjacent body tissue, to provide bonding between the host and the member, as described in detail in my copending U.S. application Ser. No. 752,603 filed Dec. 20, 1976.

The body tissue ingrowth combined with promotion of tissue growth on the porous surface from the nucleated blood stream cells is important in many applications of the principles of the present invention.

For example, in an artificial heart constructed in accordance with this invention as described above, a porous coating externally as well as internally provides a means of fixation of the artificial heart to host tissues by soft tissue ingrowth into the external porous coating as well as providing surfaces which are blood compatible arising from colonization and tissue formation on the blood-contacting surfaces.

Further, the vascular grafts provided in accordance with this invention have an outer porous layer, as described above, to provide for soft tissue ingrowth and fixation of the graft into the body.

In the case of heart pacemaker electrodes, the electrodes are mainly positioned against heart muscle which has considerable blood flow therethrough, so that the tissue growth into the surface is a combination of true soft tissue ingrowth and growth arising from the nucleated blood stream cells.

As previously mentioned, electrodes which are utilized for heart pacemaker applications are equally effective as electrodes for other stimulations within the body, such as, stimulation of the central or peripheral nervous system and muscle stimulation, by suitable placement of the electrode. The provision of a porous outer coating on the outer surface of the electrode and having the parameters described above allows soft tissue ingrowth into the outer surface to fix the electrode in place.

EXAMPLES

The invention is illustrated by the following Examples:

EXAMPLE 1

This example illustrates the formation of multiple layer porous surfaces on metal heart valve members from metal particles and the effectiveness of the coated devices in combatting thromboembolism.

Twenty-six prosthetic aortic ball valve cages were obtained and the poppets and sewing rings were removed. The metallic surfaces of fourteen of the cages were roughened, ultrasonically cleaned and coated with cobalt-base alloy powders (Vitallium) of various particle sizes to a depth of from about 100 to about 300 microns using the temperatures and times outlined in the following Table I:

TABLE I

| Powder Size | | No. of cages | Temperature | Time |
|---|---|---|---|---|
| Mesh | ($\mu$) | | | |
| −500 | less than 20 | 2 | About 2200° F. (1200° C.) | 1 hr |
| −325 +500 | 20 to 50 | 6 | About 2330° F. (1220° C.) | 2½ hrs |
| −100 +325 | 50 to 200 | 6 | About 2330° F. (1220° C.) | 2½ hrs |

The cages were implanted in the right atria of thirteen dogs, six of the dogs having implanted +500 mesh coated cages, one of the dogs having implanted the −500 mesh coated cages and the remaining six dogs having implanted uncoated cages as controls. The seating ring of each valve cage was fastened to the orifice of either the superior vena cava (SVC) or inferior vena cava (IVC) by an encircling umbilical tape such that the valve struts and their trifurcation were freely suspended in the right atrial cavity. No anticoagulants were given to any of the dogs.

One experimental dog and one control dog were sacrificed at 2 weeks, 1 month, 6 weeks, 2 months, 3 months and 6 months after implantation. Upon removal, each valve cage was examined grossly for evidence of tissue growth as well as thrombus formation. The thrombus formation was graded on a scale of 0 to ++++, 0 representing a total absence of thrombus and ++++ representing total occlusion of the valve cage orifice by thrombus.

Additionally, the lungs were examined grossly for evidence of pulmonary embolism and representative sections of each lobe were taken for light microscopy.

At each time interval, one valve cage was examined by scanning electron microscopy and a special thin section of the other valve cage was prepared for light microscopy using a low-speed diamond cut-off wheel. After the sections had been prepared, the tissue component was stained with a dilute solution of methylene blue.

The experimental dog containing the 2 valve cages with the −500 mesh powder-made metal surface was sacrificed at 2 months. The tissue covering was torn off a portion of one of the valve struts and this area, as well as an area where the tissue covering remained intact, were examined by scanning electron microscopy. A special thin section was prepared from the second valve cage as described above, and is shown in FIG. 5.

All the porous-coated valve cages were found to have developed a thin, semi-transparent, smooth, firmly attached tissue covering with absolutely no evidence of thrombosis or embolism to the lungs. In most instances, the seating ring and base of the struts were totally incorporated into the walls of either the SVC or IVC at their points of attachment. In contrast, no tissue growth occurred on the uncoated valve struts and varying degrees of thrombus formation were observed in 10 of the 12 control valve cages. Additionally there was gross and microscopic evidence of pulmonary embolism in the control dogs sacrificed at 2 weeks, 6 weeks, and 3 months.

The results are reproduced in the following Table II:

TABLE II

| | Dog Number | Site | Particle Size (Microns) | Implant Time (months) | Thrombus Formation |
|---|---|---|---|---|---|
| Experimental | 1 | SVC | 50 to 200 | 0.5 | 0 |
| | | IVC | 20 to 50 | 0.5 | 0 |
| | 2 | SVC | 20 to 50 | 1.0 | 0 |
| | | IVC | 50 to 200 | 1.0 | 0 |
| | 3 | SVC | 50 to 200 | 1.5 | 0 |
| | | IVC | 20 to 50 | 1.5 | 0 |
| | 4 | SVC | 20 to 50 | 2.0 | 0 |
| | | IVC | 50 to 200 | 2.0 | 0 |
| | 5 | SVC | 50 to 200 | 3.0 | 0 |
| | | IVC | 20 to 50 | 3.0 | 0 |
| | 6 | SVC | 20 to 50 | 6.0 | 0 |
| | | IVC | 50 to 200 | 6.0 | 0 |
| Control | 7 | SVC | uncoated | 0.5 | +++ |
| | | IVC | uncoated | 0.5 | ++++ |
| | 8 | SVC | uncoated | 1.0 | 0 |
| | | IVC | uncoated | 1.0 | + |
| | 9 | SVC | uncoated | 1.5 | ++ |
| | | IVC | uncoated | 1.5 | + |
| | 10 | SVC | uncoated | 2.0 | + |
| | | IVC | uncoated | 2.0 | 0 |
| | 11 | SVC | uncoated | 3.0 | + |
| | | IVC | uncoated | 3.0 | ++ |
| | 12 | SVC | uncoated | 6.0 | ++ |
| | | IVC | uncoated | 6.0 | ++ |

Figure 6:
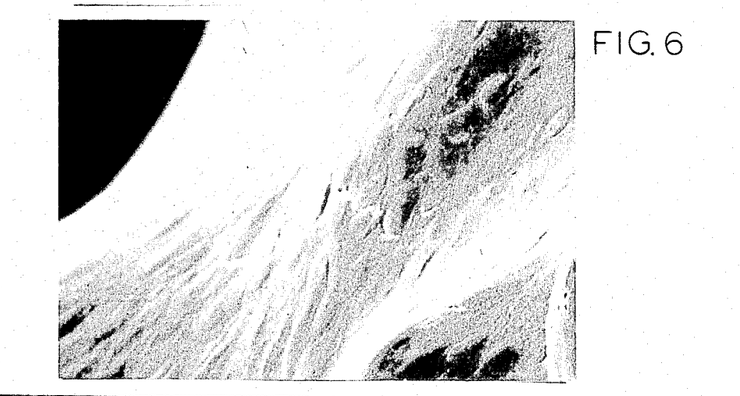
FIG. 6 is an electron micrograph of the tissue surface of composite porous coated metal body after positioning in the blood stream of a dog for 3 months at 700 times magnification showing endothelial cells in the tissue.

Scanning electron microscopy of the porous surfaces of the experimental valve cages showed a complete tissue covering as early as 2 weeks with the appearance of surface endothelial-like cells at 3 months as illustrated in FIG. 6. The undulations in the tissue covering produced by the underlying spherical metal particles in both the coarse and medium powder-made surfaces were virtually eliminated by using the fine powder-made surface (particle size −500 mesh), as can be seen from FIG. 5.

Examination of the region in which the tissue covering was torn off the fine powder-made metal surface showed that the tissue had sheared off at the surface of the porous coating leaving fragments of tissue still affixed to the underlying pore structure.

Light microscopy of the thin sections of the porous-coated struts showed the following evolution of the tissue covering. At 2 weeks the porous coating was covered with a material which resembled a platelet-fibrin mesh. Within this mesh were large mononuclear cells which have the ability to differentiate into other cell types. By 6 weeks, fibroblast-like cells had appeared and the porous coating was infiltrated and covered with connective tissue which was loosely textured within the porous coating and more compact towards the surface. Sections examined at 2 months showed well organized connective tissue within and over the surface of the porous coating. Pigment-filled macrophages had appeared and on the outer surface there were flattened endothelial-like cells. By 3 months, there was a uniform layer of connective tissue which covered the entire surface of the porous metal coating and which was quite compact even in its deeper layers. Again the surface was seen to be covered by flattened endothelial-like cells. Although some blood vessels were observed near the base of the struts where they had been in contact with the caval walls, no blood vessels were present in the tissue covering the struts which were freely suspended within the right atrial cavity. It would appear that the tissue growing on the valve struts was nourished by diffusion from the bloodstream and, as such, can survive without a blood vessel supply from the host.

Finally, the thickness of the tissue over and above the porous coating reached a maximum thickness of about 100μ which was independent of the underlying coating particle size.

EXAMPLE 2

A heart valve cage was coated with −325 +500 mesh Vitallium powder as described in Example 1 and was positioned in the descending thoracic aorta of a dog. After 6 months the dog was sacrificed. There was no evidence of major thromboembolism and the surfaces of the cage exposed to the blood stream had developed a thin, semi-transparent, smooth, firmly-attached tissue covering.

From a comparison of the results of Examples 1 and 2, it is apparent that endothelialization may occur independent of blood oxygen concentration and blood pressure.

EXAMPLE 3

This example illustrates the formation of a porous metal coating on metal parts using metal compound particles.

The surfaces of two titanium metal rods were roughened, ultrasonically cleaned and coated with a binder. Titanium hydride particles of −325 mesh were applied to the surface from a fluidized bed to a thickness of about 100 microns.

One of the rods was heated for ½ hour at about 1100° C. under a vacuum of 1 to $2 \times 10^{-5}$ torr to form a porous titanium metal coating. The other of the rods was heated for ½ hour at about 1200° C. under a vacuum of $10^{-5}$ to $10^{-6}$ torr to form a porous titanium metal coating.

Microscopic examination of sections of the coated cages revealed particle-to-particle fusion, fusion to the substrate and a uniform distribution of interconnected pores throughout the porous coating. The coating porosity was estimated to be about 30 vol %.

The coating of the first-mentioned coated rod exhibited a shear strength greater than about 1500 psi while the coating of the second-mentioned coated rod exhibited a shear strength greater than about 2000 psi.

EXAMPLE 4

This example illustrates the effectiveness of a rigid porous polymeric coating in combatting the incidence of thromboembolism.

A composite of a polymethyl methacrylate powder and a coherent polymethyl methacrylate base was mounted to the strut of a porous metal coated heart valve cage and placed in the right atrium of a dog. After one year, the dog was still alive and well, indicating probable endothelialization of the polymethyl methacrylate porous surface.

EXAMPLE 5

This example illustrates the formation of flexible porous polymer products.

A 20% solution of a hydrophilic segmented polyetherpolyurethane urea block copolymer in dimethyl formamide and containing 4 g of polymer was slurried with 10 g of sodium chloride crystals of average size −200 +500 mesh. The slurry was dried in a vacuum oven to remove the solvent. The polymer coated salt was placed in a mold and compression molded at 300° to 350° F. (150° to 175° C.) for about 15 minutes. The mold was cooled and the sample removed.

Figure 7:
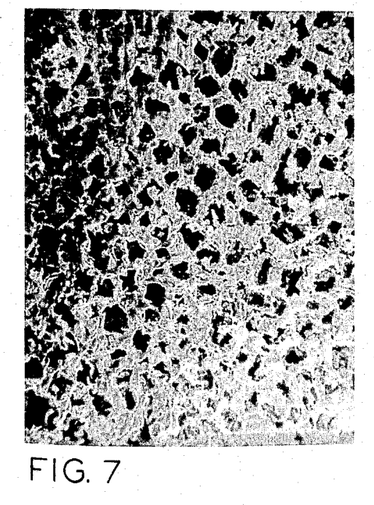
FIG. 7 is a photograph of a porous hydrophilic polyurethane element at 20 times magnification.
Figure 8:
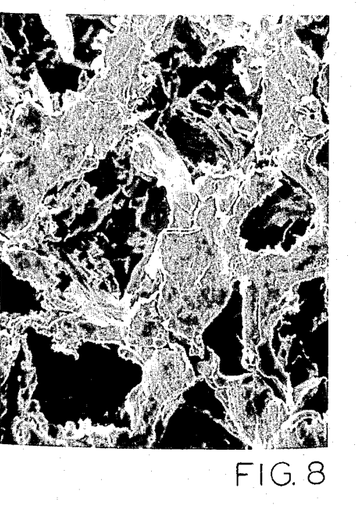
FIG. 8 is a photograph of the porous surface of FIG. 7 at 100 times magnification.
Figure 9:
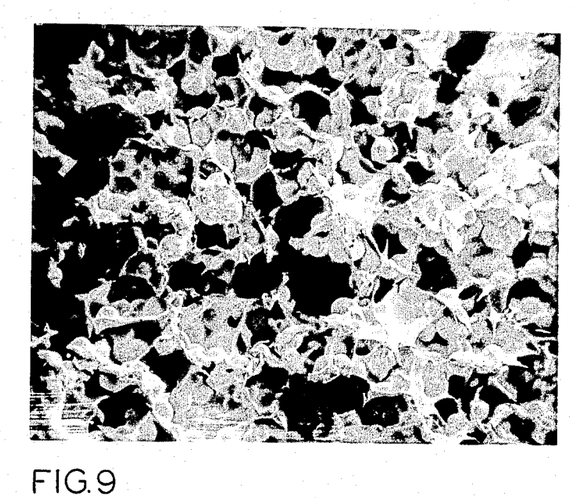
FIG. 9 is a photograph of a porous polymethylmethacrylate surface at 17 times magnification.
Figure 10:
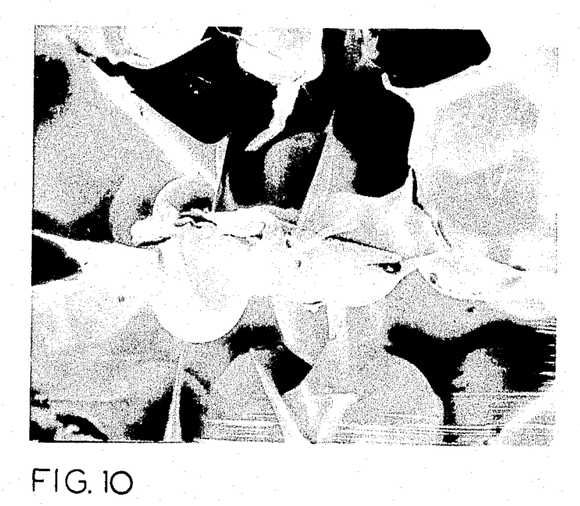
FIG. 10 is a photograph of the porous surface of FIG. 9 at 90 times magnification
Figures 11, 12:
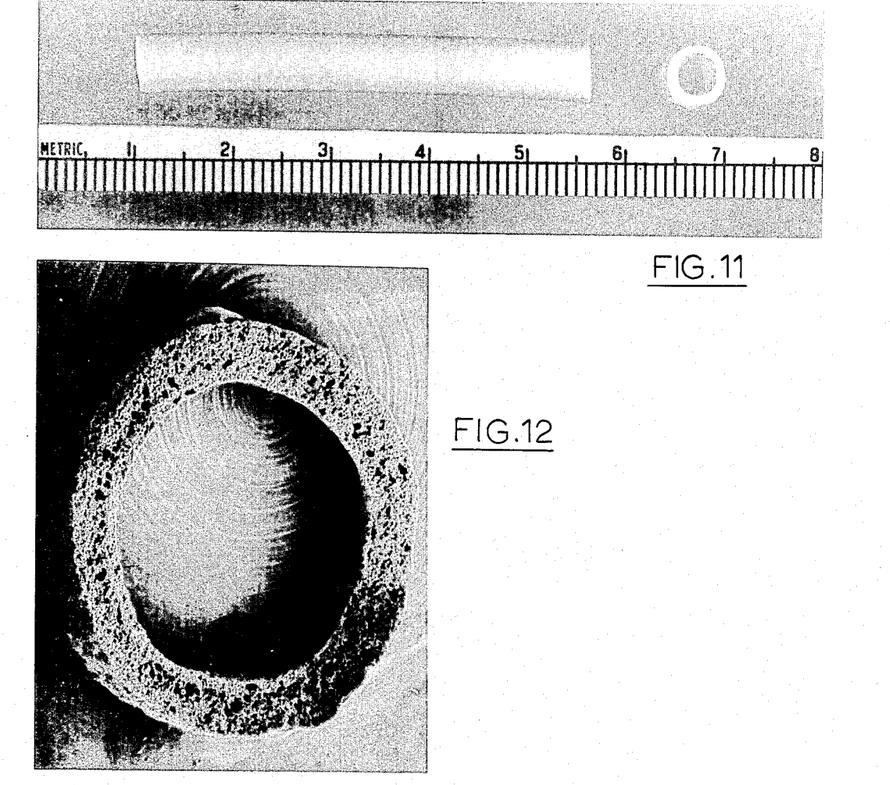
FIG. 11 is a full scale photograph of a microporous hydrophilic polyurethane vascular graft provided in accordance with the invention.
FIG. 12 is a photograph of a cut section of the tube shown in FIG. 11 at 16 times magnification.
Figure 13:
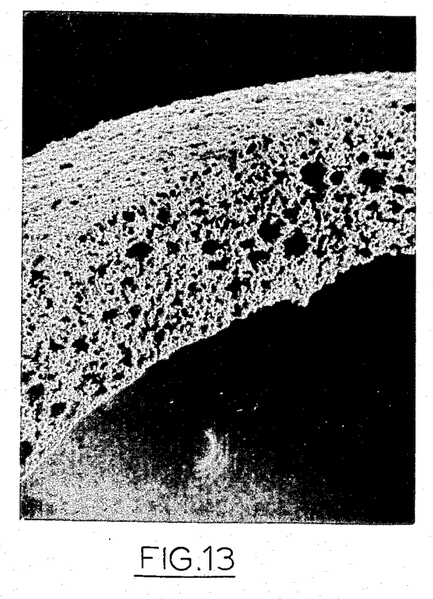
FIG. 13 is a photograph of a cut section of the tube shown in FIG. 11 at 50 times magnification.
Figure 14:
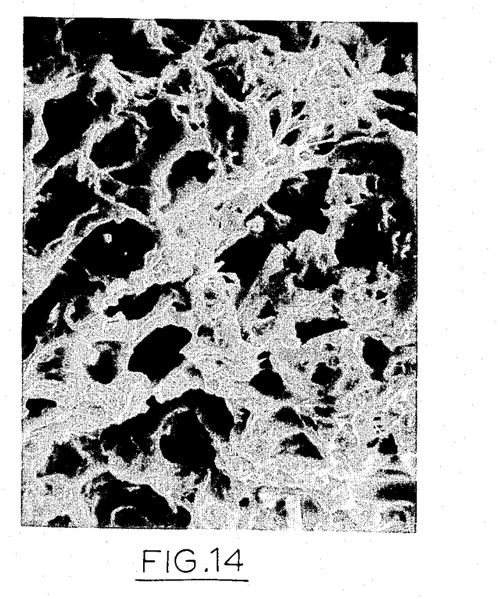
FIG. 14 is a photograph of a cut section of the tube shown in FIG. 11 at 1000 times magnification.

After removal from the mold, the sample was immersed in a beaker of hot water and squeezed from time to time to assist in salt removal. After completion of the salt leaching, a porous spongy polymer product with interconnected pores resulted. The product had the microscopic appearance seen in FIGS. 7 and 8.

EXAMPLE 6

This example illustrates the formation of a small bore vascular graft.

A 30% solution of a hydrophilic segmented polyether-polyurethane urea block copolymer in dimethyl formamide was mixed with sodium chloride crystals of average size −200 +300 mesh in a 1:1 weight ratio of sodium chloride to polymer to form a viscous solution. The solution was positioned in a glass tube of inside diameter 6 mm and the tube was allowed to pass a conically-shaped plumb ball of maximum diameter approximately 4 mm attached to the lower end of a string to cast a polymer tube inside the glass tube.

After drying under an infrared heating lamp, the polymer tube was removed from the glass tube by immersion in water and annealed by boiling in the water. The operations of immersion and annealing also resulted in leaching of the sodium chloride from the tube to form a wholly porous microporous tube. Photographs of the tube at various magnifications are shown in FIGS. 11 to 14.

EXAMPLE 7

This example illustrates the formation of a fabric layer reinforced small bore vascular graft.

Figure 15:
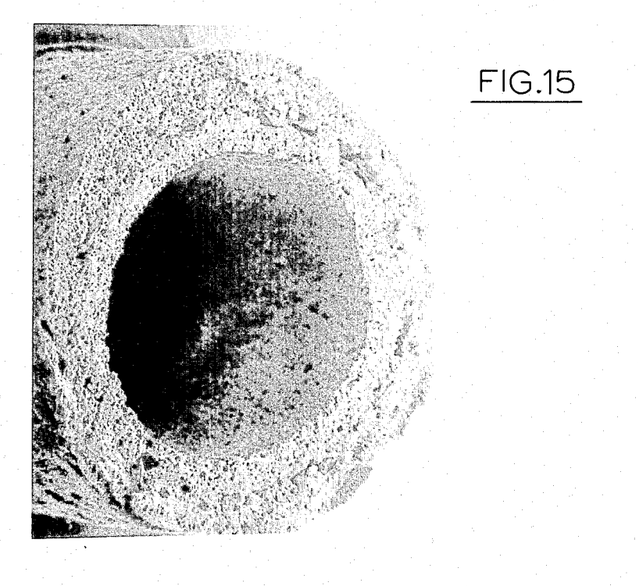
FIG. 15 is a photograph of a cut section of a porous tube similar to that shown in FIG. 11 having a woven fabric reinforcing core at 18 times magnification.
Figure 16:
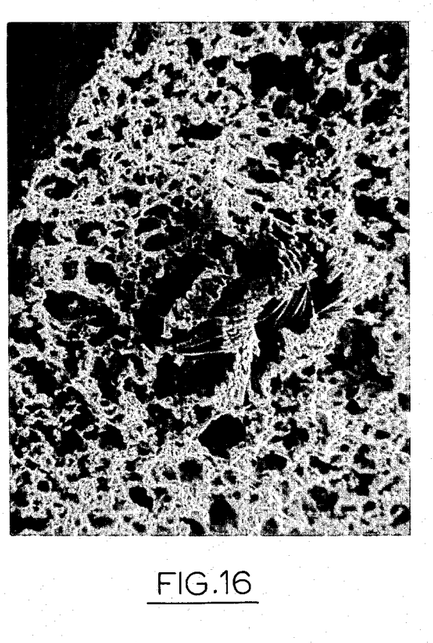
FIG. 16 is a photograph of the cut section of FIG. 15 at 200 times magnification.
Figure 17:
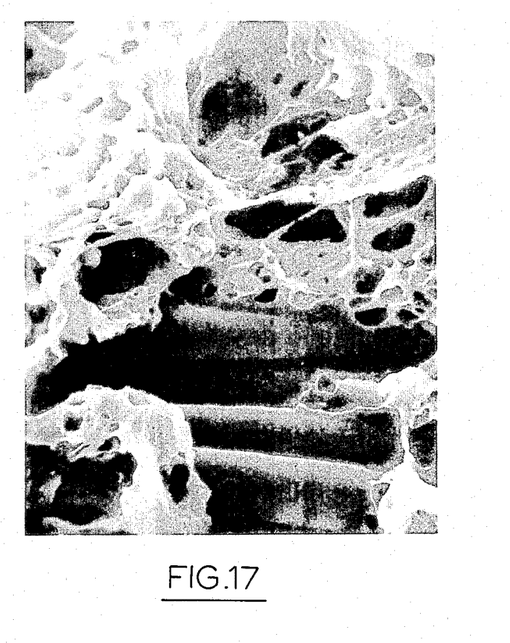
FIG. 17 is a photograph of the cut section of FIG. 15 at 1000 times magnification.

The procedure of Example 6 was repeated with the exception that a knitted Dacron fabric was positioned in the polymer tube to provide reinforcement thereto. Photographs of the resulting tube at various magnifications are shown in FIGS. 15 to 17.

SUMMARY

The present invention, therefore, provides novel cardiovascular devices or implants which have biocompatibility and avoid the prior art thrombogenic problems. Modifications are possible within the scope of the invention.

What I claim is:

1. A blood stream controlled release device comprising a hollow chamber containing a source of material to be released to blood and a porous surface of said chamber adapted to interface with a blood stream to establish communication between the blood stream and the interior of the chamber to permit said material release into the blood through a network of interconnected pores, said porous surface being formed of rigid material inert to blood and selected from metals, polymeric materials, ceramics and carbon, said porous surface having a porosity of at least 8% by volume up to the limit of coherence of the surface, an interstitial pore size of about 1 to about 1000 microns and a thickness up to 1 cm.

2. The device of claim 1 wherein said substance is a hormone or a drug.

3. The device of claim 1 wherein said porosity is about 10 to about 50% by volume and said thickness is about 25 to about 500 microns.

4. A method for the control of the release of substances into the blood stream, which comprises positioning a cardiovascular implant in the blood stream, said implant having a porous surface interfacing the blood and a network of interconnected pores in a subsurface in fluid flow communication with the porous surface, providing a source of a substance to be released into the blood in fluid flow communication with said subsurface on the opposite side thereof from said blood-interfacing surface, and releasing said substance through said subsurface and tissue growth on said blood-interfacing surface into said blood stream.

5. The method of claim 4 wherein said substance is a drug or a hormone.

* * * * *